United States Patent [19]

Krumme

[11] 4,259,584
[45] Mar. 31, 1981

[54] APPARATUS FOR TRANSMITTING SIGNALS
[75] Inventor: Hans J. Krumme, Uttenreuth, Fed. Rep. of Germany
[73] Assignee: Siemens Aktiengesellschaft, Berlin & Munich, Fed. Rep. of Germany
[21] Appl. No.: 78,052
[22] Filed: Sep. 24, 1979
[30] Foreign Application Priority Data
Oct. 25, 1978 [DE] Fed. Rep. of Germany ....... 2846526
[51] Int. Cl.$^3$ ............................................ G03B 41/16
[52] U.S. Cl. ................................. 250/445 T; 250/368
[58] Field of Search ................... 250/445 T, 361, 362, 250/363, 363 S, 368

[56] References Cited
U.S. PATENT DOCUMENTS
4,031,395  6/1977  LeMay ............................ 250/445 T Primary Examiner—Craig E. Church
Attorney, Agent, or Firm—Hill, Van Santen, Steadman, Chiara & Simpson

[57] ABSTRACT

In the exemplary embodiments, a ring made of light-conductive material curved around the center of rotation is provided, onto the surface of which a light source radiates, which emits light signals corresponding to the signals to be transmitted. The light-conductive ring is formed in such a manner that it passes on the incident light over its entire periphery and has at least one point of interruption on which a light receiver is arranged. The invention is particularly suited for use in a computer-tomograph, in which an x-ray source and a detector for scanning the radiography subject at different projections rotate around the radiography subject, and data processing equipment determine an image of the examined transverse layer of the radiography subject from the detector signals. In this case the light-conductive ring can transmit the detector signals to the stationary part.

8 Claims, 6 Drawing Figures

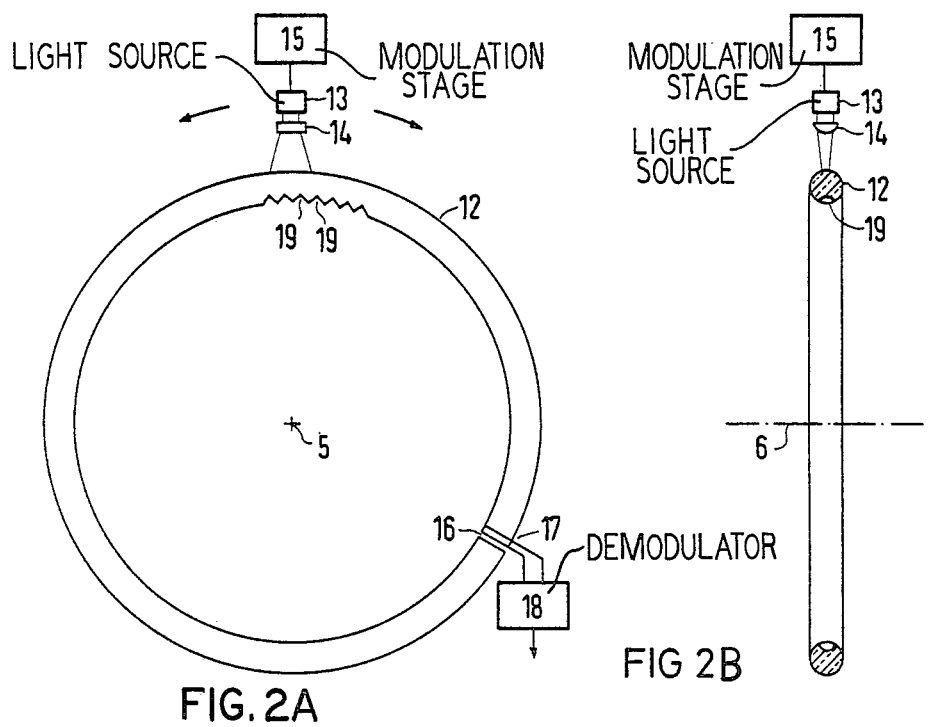
FIG. 2A
FIG 2B
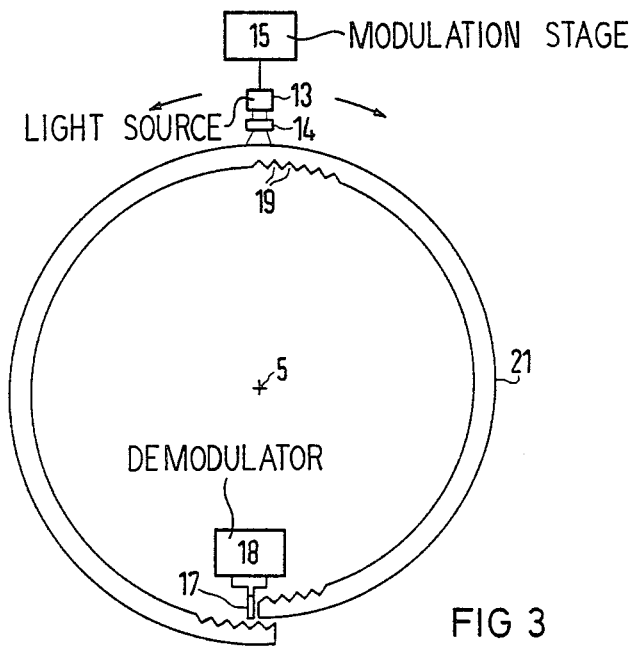
FIG 3

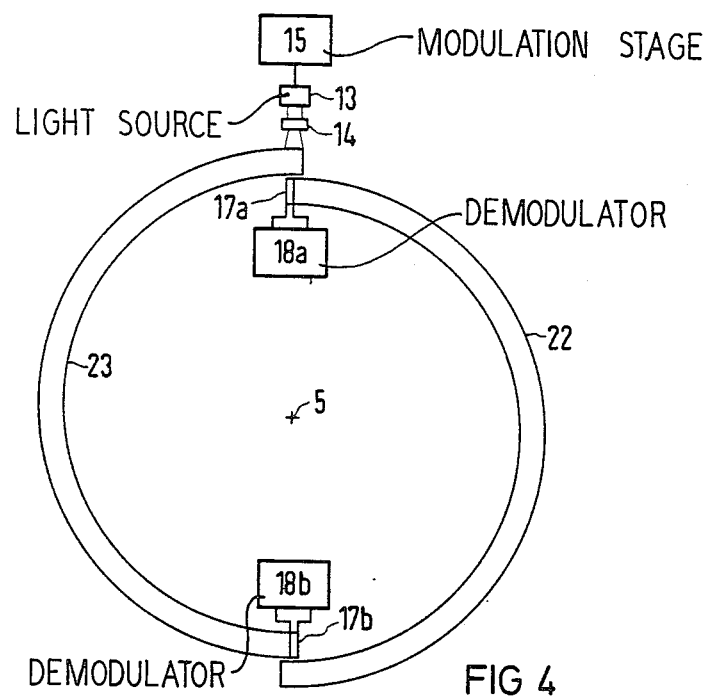
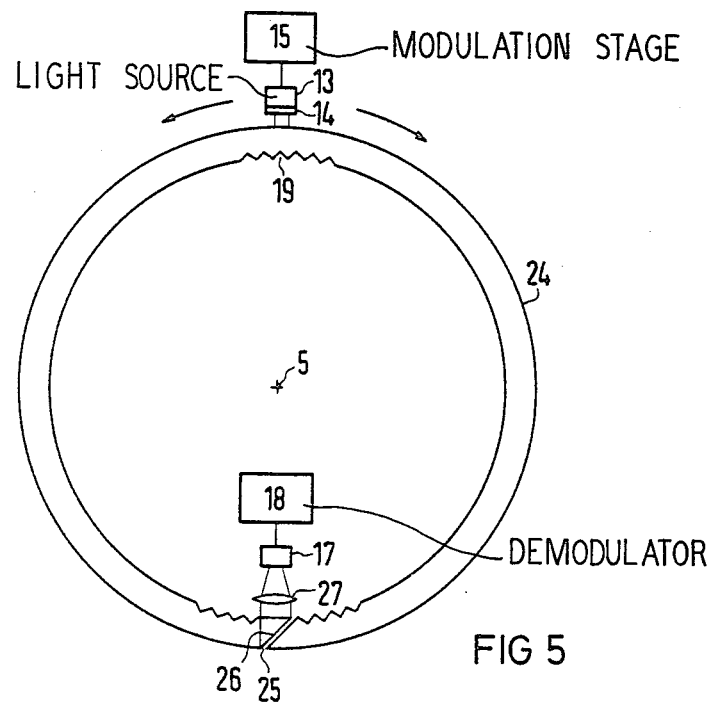

APPARATUS FOR TRANSMITTING SIGNALS

BACKGROUND OF THE INVENTION

The invention relates to an apparatus for transmitting signals between a rotating and a stationary part.

An apparatus of this kind is desirable for example in an x-ray examination device in which case the patient is scanned by means of a measuring arrangement consisting of an x-ray tube and a radiation detector at different projections and the attenuation coefficients of the examined layer of the patient are determined from the output signals of the detector. In a computer-tomograph of this kind, the examination time is determined essentially by the scanning time of the measuring arrangement. It is known to revolve the measuring arrangement by an angle of 360° around the patient for a scanning procedure and subsequently to return it to its starting position for the next scanning procedure. In this case the detector can be connected to the electronics which process the measured values by way of cables. However the times required for accelerating the measuring arrangement limit the scanning time. It would be possible to shorten the scanning time if the measuring arrangement were to rotate continuously. In this case cables would no longer have to be used for the x-ray tube or the detector for the purpose of supplying current or removing signals respectively. The supply to the x-ray tube can take place for example by way of slip rings. However in this case neither slip rings nor inductive transformers can be considered for detecting the signals of the detector because of the high data rate and the requisite freedom from interference. In order to economize on the expensive temporary memory on the rotating part, the data transmission must take place at least exactly as quickly as the data collection. Hence very high speeds of approximately one to thirty megabits per second (1 to 30 mbit/sec) are suitable.

SUMMARY OF THE INVENTION

The object of the invention is to produce an apparatus of the type mentioned in the introduction which allows data to be transmitted in an extremely short time in an interference- and contact-free manner.

This object is achieved according to the invention by means of a ring made of light-conductive material curved around the center of rotation, onto the surface of which a light source radiates, which emits corresponding light signals to the signals to be transmitted, said ring being formed in such a manner that it passes on the incident light over its entire periphery and has at least one coupling point at which a light receiver is arranged. An object can be inserted thereby into the ring without disturbing the data transmission. Therefore the apparatus is particularly suited to data transmission in a computer-tomograph of the type mentioned in the introduction, in which case the ring encloses the patient. It can remain stationary thereby while the data from the detector is transmitted by way of the light source in the form of light pulses. The reverse case is also possible, i.e. a stationary light source and a rotating ring with rotating light receiver for transmitting data to a rotating part, i.e. to the rotating x-ray tube of a computer-tomograph.

Details of the invention are to be found in the subclaims.

The invention is explained in greater detail as follows in conjunction with some exemplary embodiments represented in the drawings; and other objects, features and advantages will be apparent from this detailed disclosure and from the appended claims.

BRIEF DESCRIPTION OF THE DRAWINGS

FIGS. 2 to 5 show four exemplary embodiments of an apparatus according to the invention.

DETAILED DESCRIPTION

Figure 1:
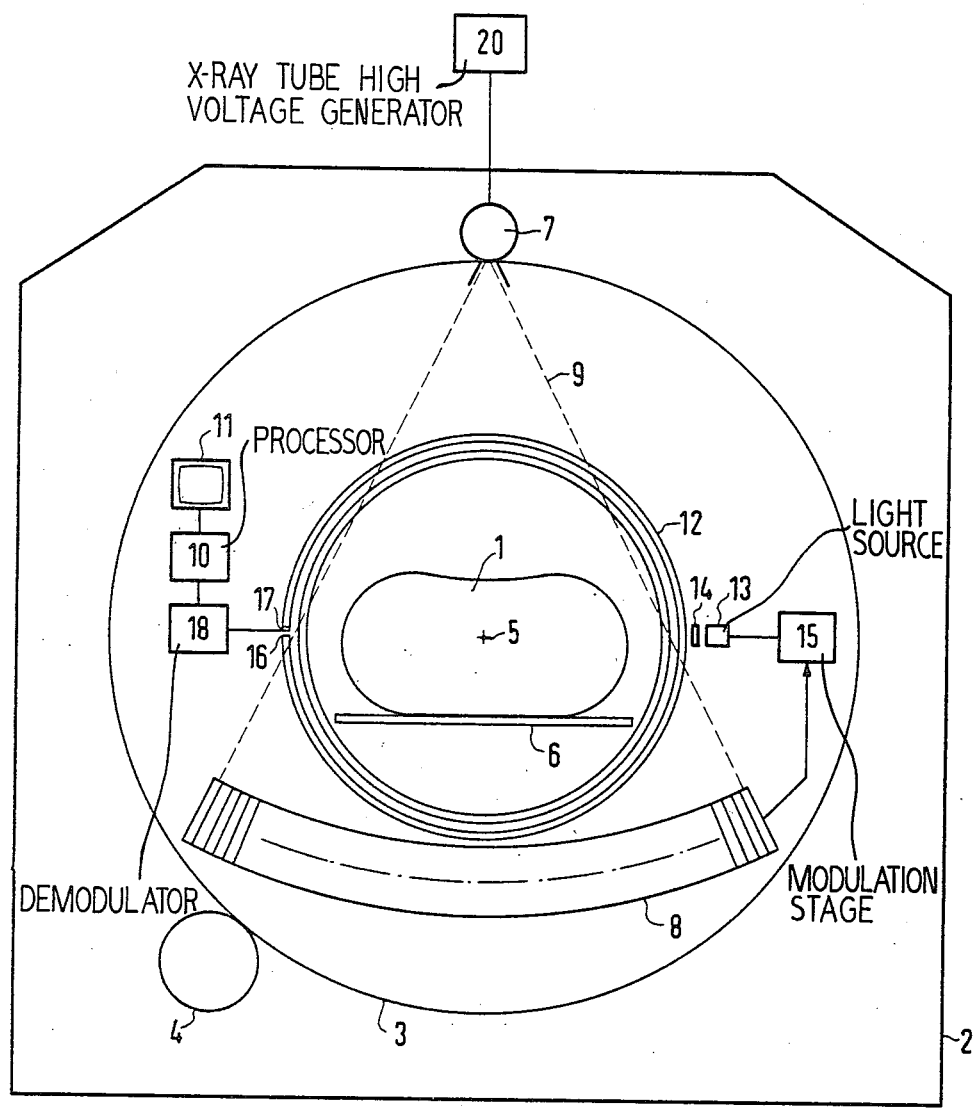
FIG. 1 shows a computer-tomograph for explaining the concept of the invention.

FIG. 1 shows an x-ray diagnostic unit for producing transverse layer images of a patient 1, a so-called computer-tomograph. The apparatus has a rotatable support 3 in a frame 2, said support being rotatable about an axis 5 running perpendicular to the plane of the drawing by means of a motor 4. An x-ray tube 7 and a detector 8 for x-ray radiation are provided for scanning the patient 1 lying on a support 6. The x-ray tube 7 emits a fan-shaped x-ray radiation beam 9, the extent of which is chosen so that the entire transverse layer of the patient 1 which is to be examined is penetrated by x-ray radiation. The thickness of the x-ray radiation beam 9 perpendicular to the plane of the layer is equal to the thickness of the layer, i.e. a few millimeters.

In order to scan the patient 1, the measuring arrangement, consisting of x-ray tube 7 and detector 8 is rotated about the patient 1 by an angle of approximately 360° and at predetermined projections, e.g. at each angular degree a set of output signals of the detector 8 is read. The detector 8 consists of a series of single detectors, e.g. 256 single detectors, so that for example 256 signals of the detector 8 are read per projection and for example 360×256 signals are available for processing per scanning procedure. The signals are transmitted in the manner described in greater detail hereinafter to a stationary data processing device 10 which determines from these the attenuation values of predetermined points in the examined transverse layer of the patient 1 in the form of a matrix and effects the image reproduction on a monitor 11.

A stationary ring 12 made of light-conductive material, e.g. synthetic glass, curved around the axis of rotation 5, is provided for transmitting the detector signals, onto the surface of which a light source 13 radiates by way of optics 14. The light source 13 is connected to a modulation stage 15, which converts the detector signals into sequential light-producing signals. A pulse spacing coding can be used thereby for example. The ring 12 is formed in such a manner that the light from the light source 13 is passed on over its entire periphery. It has a gap 16 and a light receiver 17, which converts the light signals into electrical signals again, is arranged on one of the faces bordering the gap. These signals are demodulated in a demodulator stage 18 and are supplied to the data processing device 10. The signal transmission takes place thereby during a projection in a consecutive manner, this means the detector signals of the single detectors are transmitted consecutively by means of the described apparatus. The light source 13 can for example be a luminescence or a laser diode working in the infrared area. The modulated stage 15, the light source 13 and the optics 14 rotate with the measuring arrangement 7, 8 while the patient is being scanned, whereas the structural elements 12, 17, 18, 10, 11 are stationary during the scanning procedure. Consequently a contact-free signal transmission takes place from a rotating part to a stationary part and the speed of rotation of the rotating part, i.e. of the rotatable support 3, can be selected to be at a very high level. In particular it is possible to allow the rotatable support 3 to rotate continuously with a great number of rotations per minute and to make a radiograph when required during an angle of rotation of approximately 360°.

In FIG. 2 the system for optical signal transmission is clearly delineated again in two views which are taken perpendicular to each other. It may be seen from FIG. 2A that the ring 12 is provided on its inside with steps 19 which extend over its entire periphery and cause a reflection of light so that the light of the light source 1 disperses uniformly over the entire periphery of the ring 12. Data transmission from the stationary part to the rotating part can also be realized with an apparatus according to FIG. 2. This transmission can be important for example for the triggering of the x-ray tube 7 which is supplied from a generator 20, the changing of collimators for the x-ray tube 7, the control of the measuring electronics, etc. In this case the ring 12 is arranged with the receiver 17 on the rotating part, and the light source 13 with the optics 14 is arranged in a stationary manner.

In the described computer-tomograph the x-ray tube 7 rotates, so that it cannot be connected directly to the generator 20 by cable. Rotating transmission means, e.g. slip rings, must be provided in this case.

The ring 12 is almost closed. Data transmission cannot take place only in the area in which the light receiver 17 is accommodated. It must be ensured with electronic means that the transmission discontinues in this place and that the measured value is not lost.

The optics 14 needs to concentrate the light only in a plane which passes through the axis 5. Therefore they can be formed from a cylindrical lens.

FIG. 3 shows a ring 21 which is formed in a slightly spiral manner, so that the two ring ends lie at the point of interruption on different radii but in a common plane. The light receiver 17 is arranged on the face of a ring end in this case also. The two ring ends overlap a little, so that the complete range of 360° can be utilized for the detection and transmission of measured values.

In the example according to FIG. 4 the ring is formed from two halves 22, 23 which are radially displaced relative to each other approximately by the width of the ring. A light receiver 17a, 17b is coupled respectively on one end in each case of a ring half on the face. A demodulator 18a, 18b is allocated respectively to each light receiver 17a, 17b. The ends of the ring halves overlap slightly in this case also. FIG. 4 is based on the concept that the rate of data to be transmitted by means of the pulse expansion of the light signals during the transmission is limited by the length of the light-conductive ring or ring part respectively. Therefore this length determines the rate of data which can be transmitted. Consequently the ring must be divided into two or even more parts for very high rates of data. Accordingly many receivers are provided. Any loss of data is prevented here also in that the parts of the ring are alternately radially displaced and arranged so that they overlap.

In the exemplary embodiment according to FIG. 5 the point of interruption of a ring 24 forms a gap 25 penetrating the ring 24 obliquely at an angle different from 90°. The face 26 provides for a deflection of the light and optics 27 supply the deflected light to the light receiver 17. Any loss of data is prevented here also because of the oblique arrangement of the gap 25.

In a modification of the exemplary embodiments a light-conductive cable, which for example may be flexible, can also be coupled to the respective faces of the light-conductive ring, said cable transmitting the light from the light-conductive ring to the receiver.

In the exemplary embodiments the steps 19 of course extend over the entire inner surface of the ring. They are shown in the drawing only over a part of this inner surface for the sake of simplicity.

In the case that the signal transmission takes place from a stationary part to the x-ray tube 7 for its control, the detector 8 of course rotates with the x-ray tube 7. The light source 13 is controlled thereby not by the signals of the detector but by a control stage for the x-ray tube 7. The light receiver corotating with the ring and the measuring arrangement controls the x-ray tube by way of control circuit stages.

It will be apparent that many modifications and variations may be effected without departing from the scope of the novel concepts and teachings of the present invention.

I claim as my invention:

1. A tomographic scanning apparatus for producing transverse layer images, comprising a measuring arrangement including an x-ray source (7) and a radiation receiver (8), a rotatable support (3) carrying the measuring arrangement so that the radiography subject (1) can be scanned at different projections by means of an x-ray radiation beam (9) emitted from the x-ray source (7), the thickness of which perpendicular to the plane of the layer to be examined being equal to the thickness of the layer, and a data processing device (10) for determining an image of the examined layer from the signals supplied by the radiation receiver (8), characterized in that an arcuate light guide made of light conductive material is curved about the center of rotation of the measuring arrangement and provides for a continuous signal coupling between rotating and stationary parts of the apparatus throughout the angular range of rotation required to effect a tomographic scanning operation, whereby the measuring arrangement can be rotating at constant speed prior to initiation of a scanning operation.

2. A tomographic scanning apparatus according to claim 1, with a light source (13) for radiating light onto the light guide and which emits light signals corresponding to the signals to be transmitted, said arcuate light guide being formed in such a manner that it passes on the incident light from the light source (13) over its entire periphery and has at least one coupling point (16, 25), and a light receiver (17, 17a, 17b) is arranged at the coupling point.

3. A tomographic scanning apparatus according to claim 1, said light guide being in the form of a ring (12) extending about the center of rotation (5), the coupling point (16) is a gap and the light receiver (17) is arranged on a face of the ring (12) bordering the gap (16).

4. A tomographic scanning apparatus according to claim 1, wherein the arcuate light guide (21) is formed in a slightly spiral manner so that the two ends lie at the coupling point on different radii and that the light receiver (17) is arranged on the face of a ring end.

5. A tomographic scanning apparatus according to claim 4, wherein the ring ends overlap slightly.

6. A tomographic scanning apparatus according to claim 1, wherein the arcuate light guide is formed from several arcuate parts (22, 23) which are radially displaced relative to each other approximately by the width thereof, and that a light receiver (17a, 17b) is coupled respectively on one end in each case of each arcuate part (22, 23).

7. A tomographic scanning apparatus according to claim 1, wherein the coupling point is a gap (25) disposed obliquely to the axis of the arcuate light guide at an angle departing from 90° and the light receiver (17) is arranged to receive the light reflected from a face (26) of the light guide (24) bordering the gap.

8. A tomographic scanning apparatus according to claim 2, wherein the light source is coupled with the radiation receiver and rotates therewith, and the arcuate light guide is stationary and is coupled with the data processing device via the light receiver during a tomographic scanning operation to effect immediate transmission of the signals supplied by the radiation receiver to the data processing device during the course of such scanning operation.

* * * * *